US009326738B2

(12) United States Patent
Yin et al.

(10) Patent No.: US 9,326,738 B2
(45) Date of Patent: May 3, 2016

(54) METHOD AND SYSTEM FOR REDUCED DOSE X-RAY IMAGING

(75) Inventors: Zhye Yin, Schenectady, NY (US); Roy Arnulf Helge Nilsen, Waukesha, WI (US); Jiahua Fan, New Berlin, WI (US); Thomas Matthew Benson, Smyrna, GA (US); Bruno Kristiaan Bernard De Man, Clifton Park, NY (US); Jed Douglas Pack, Glenville, NY (US); Kai Zeng, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 727 days.

(21) Appl. No.: 13/174,438

(22) Filed: Jun. 30, 2011

(65) Prior Publication Data

US 2013/0003914 A1 Jan. 3, 2013

(51) Int. Cl.
*A61B 6/03* (2006.01)
*A61B 6/06* (2006.01)
*A61B 6/00* (2006.01)

(52) U.S. Cl.
CPC . *A61B 6/032* (2013.01); *A61B 6/06* (2013.01); *A61B 6/405* (2013.01); *A61B 6/4085* (2013.01); *A61B 6/4435* (2013.01); *A61B 6/542* (2013.01)

(58) Field of Classification Search
CPC ................................. A61B 6/405; A61B 6/542
See application file for complete search history.

(56) References Cited

U.S. PATENT DOCUMENTS

| 5,379,333 | A | 1/1995 | Toth |
| 5,450,462 | A | 9/1995 | Toth et al. |
| 5,485,494 | A | 1/1996 | Williams et al. |
| 5,625,662 | A | 4/1997 | Toth et al. |
| 5,867,555 | A * | 2/1999 | Popescu et al. ................. 378/16 |
| 6,298,111 | B1 * | 10/2001 | Ozaki ................................ 378/8 |
| 6,307,910 | B1 * | 10/2001 | Acharya et al. .................. 378/4 |
| 6,507,639 | B1 | 1/2003 | Popescu |
| 7,068,750 | B2 | 6/2006 | Toth et al. |
| 7,313,217 | B2 | 12/2007 | Toth et al. |
| 7,558,364 | B2 * | 7/2009 | Lin ................................. 378/16 |
| 7,636,415 | B2 | 12/2009 | Popescu et al. |
| 2003/0185343 | A1 * | 10/2003 | Horiuchi ...................... 378/108 |
| 2004/0062341 | A1 | 4/2004 | Popescu et al. |
| 2004/0086076 | A1 * | 5/2004 | Nagaoka et al. .................. 378/4 |

(Continued)

FOREIGN PATENT DOCUMENTS

| DE | 102007008118 A1 | 8/2008 |
| DE | 102007013352 A1 | 9/2008 |

(Continued)

OTHER PUBLICATIONS

McCollough, Cyntha H., Ph.D., et al.; "CT Dose Reduction and Dose Management Tools: Overview of Available Options"; RadioGraphics, Mar.-Apr. 2006 vol. 26, No. 2, pp. 503-512.

(Continued)

*Primary Examiner* — David J Makiya
*Assistant Examiner* — Dani Fox
(74) *Attorney, Agent, or Firm* — Pabrita K. Chakrabarti (57) ABSTRACT

Approaches for acquiring CT image data corresponding to a full scan, but at a reduced dose are disclosed. In one implementation, X-ray tube current modulation is employed to reduce the effective dose. In other implementations, acquisition of sparse views, z-collimation, and two-rotation acquisition protocols may be employed to achieve a reduced dose relative to a full-scan acquisition protocol.

17 Claims, 5 Drawing Sheets

(56) References Cited

U.S. PATENT DOCUMENTS

| | | |
|---|---|---|
| 2005/0053188 A1* | 3/2005 | Gohno .............................. 378/15 |
| 2005/0185759 A1 | 8/2005 | Toth et al. |
| 2005/0185760 A1* | 8/2005 | Suzuki .......................... 378/109 |
| 2010/0303196 A1 | 12/2010 | Zou |
| 2011/0026668 A1 | 2/2011 | Wu et al. |
| 2012/0106695 A1* | 5/2012 | Fan et al. ........................... 378/8 |

FOREIGN PATENT DOCUMENTS

| | | |
|---|---|---|
| EP | 1547524 A1 | 6/2005 |
| EP | 1762176 A2 | 3/2007 |
| WO | 2010070583 A1 | 6/2010 |
| WO | 2010087267 A1 | 8/2010 |

OTHER PUBLICATIONS

Gies, Michael, et al.; "Dose reduction in CT by anatomically adapted tube current modulation"; Med.Phys. vol. 26, No. 11, Nov. 1999, pp. 2235-2247.

Unofficial English translation of NL Search Report and Written Opinion issued Apr. 2, 2014 in connection with corresponding NL Patent Application No. 2009071.

\* cited by examiner

METHOD AND SYSTEM FOR REDUCED DOSE X-RAY IMAGING

BACKGROUND

Non-invasive imaging technologies allow images of the internal structures of a patient or object to be obtained without performing an invasive procedure on the patient or object. In particular, technologies such as computed tomography (CT) use various physical principles, such as the differential transmission of X-rays through the target volume, to acquire image data and to construct tomographic images (e.g., three-dimensional representations of the interior of the human body or of other imaged structures).

However, imaging techniques based on the exposure of the patient to X-rays may be balanced between the desirability for obtaining as much useful image data as possible and the desirability of minimizing or reducing the patient's exposure to X-rays to the extent feasible. That is, the dose of X-rays to which the patient is exposed may constrain the types and/or amount of image data that is acquired. As a result imaging protocols that may be deemed useful in certain contexts or for certain pathologies (such as cardiac or angiography applications) may be undesirable for dosage reasons.

BRIEF DESCRIPTION

In one embodiment, a method of image data acquisition is provided. In accordance with this method, an X-ray source is rotated at least through a full rotation about an imaging volume. An operating current of the X-ray source is modulated during the full rotation so that a portion of the full rotation generally corresponding to a half-scan occurs at a higher operating current than a remainder portion of the full rotation. X-ray transmission data is acquired as the X-ray source is rotated about the imaging volume.

In a further embodiment, a method of image data acquisition on a CT imaging system is provided. In accordance with this method, an X-ray source of the CT imaging system is rotated at least through one full rotation about an imaging volume. Image data corresponding to a full-scan is acquired during the rotation of the X-ray source about the imaging volume. A dose associated with the acquisition of the image data is less than a corresponding dose associated with performing a full-scan on the CT imaging system at a constant operating current of the X-ray source.

In another embodiment, a CT imaging system is provided. The CT imaging system comprises an X-ray source configured to rotate about an imaging volume and a detector configured to detect X-rays emitted by the X-ray source. The CT imaging system also comprises a system controller configured to control operation of one or both of the X-ray source and the detector. The system controller rotates the X-ray source at least through one full rotation about the imaging volume and acquires image data corresponding to a full-scan during the rotation of the X-ray source about the imaging volume. A dose associated with the acquisition of the image data is less than a corresponding dose associated with performing a full-scan on the CT imaging system at a constant operating current of the X-ray source.

BRIEF DESCRIPTION OF THE DRAWINGS

These and other features and aspects of embodiments of the present invention will become better understood when the following detailed description is read with reference to the accompanying drawings in which like characters represent like parts throughout the drawings, wherein.

DETAILED DESCRIPTION

In certain imaging protocols, such as wide-cone axial cardiac CT reconstructions, a full-scan (i.e., a 360° rotation worth of image data plus some possible overlap) of image data may be acquired so as to minimize cone-beam artifacts while maintaining the same temporal resolution as a conventional half-scan (i.e., a 180° partial rotation plus the cone or fan angle of the X-ray beam). Other scan protocols may also benefit from the acquisition of 360° worth of views, such as to reduce artifacts or to otherwise have a more complete data set. Since such full-scan implementations acquire 360° worth of views, the X-ray dose compared to a conventional half-scan increases by about 50%.

Embodiments disclosed herein relate to various approaches for reducing patient X-ray dose while obtaining desired types and/or amounts of X-ray image data, such as full-scan, wide-cone data acquisitions. In certain such embodiments a full-scan of data may be obtained at a reduced dose by employing mA modulation during the image data acquisition. In other approaches, sparse view acquisitions may be employed to stay below a given dose while acquiring image data, such as a full-scan of cone-beam data. Likewise, 2-rotation protocols and/or z-collimation may be employed in such scenarios. In such approaches, a full-scan of image data (such as cardiac CT image data) may be acquired at a suitable dose level of X-rays.

Figure 1:
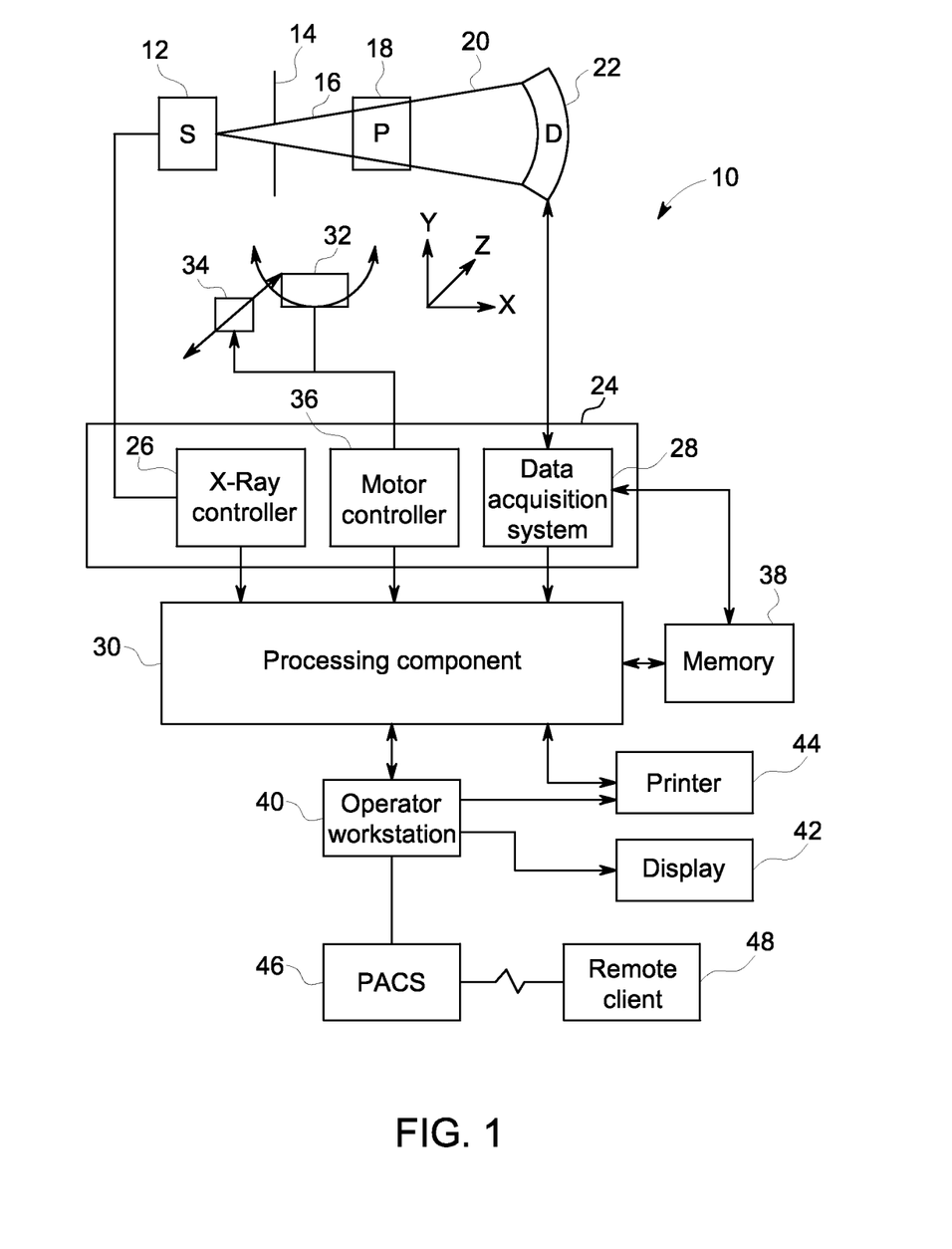
FIG. 1 is a diagrammatical view of a CT imaging system for use in producing images in accordance with aspects of the present disclosure.

With this in mind, an example of a computer tomography (CT) imaging system 10 suitable for acquiring X-ray attenuation data at a variety of views around a patient (or other subject or object of interest) in accordance with the present approaches and suitable for tomographic image reconstruction is provided in FIG. 1. In the embodiment illustrated in FIG. 1, imaging system 10 includes a source of X-ray radiation 12 positioned adjacent to a collimator 14. The X-ray source 12 may be an X-ray tube, a distributed X-ray source (such as a solid-state or thermionic X-ray source) or any other source of X-ray radiation suitable for the acquisition of medical or other images.

The collimator 14 permits X-rays 16 to pass into a region in which a patient 18, is positioned. In the depicted example, the X-rays 16 are collimated to be a cone-shaped beam, i.e., a cone-beam, that passes through the imaged volume. A portion of the X-ray radiation 20 passes through or around the patient 18 (or other subject of interest) and impacts a detector array, represented generally at reference numeral 22. Detector elements of the array produce electrical signals that represent the intensity of the incident X-rays 20. These signals are acquired and processed to reconstruct images of the features within the patient 18.

Source 12 is controlled by a system controller 24, which furnishes both power, and control signals for CT examination sequences. In the depicted embodiment, the system controller 24 controls the source 12 via an X-ray controller 26 which may be a component of the system controller 24. In such an embodiment, the X-ray controller 26 may be configured to provide power and timing signals to the X-ray source 12.

Moreover, the detector 22 is coupled to the system controller 24, which controls acquisition of the signals generated in the detector 22. In the depicted embodiment, the system controller 24 acquires the signals generated by the detector using a data acquisition system 28. The data acquisition system 28 receives data collected by readout electronics of the detector 22. The data acquisition system 28 may receive sampled analog signals from the detector 22 and convert the data to digital signals for subsequent processing by a processor 30 discussed below. Alternatively, in other embodiments the digital-to-analog conversion may be performed by circuitry provided on the detector 22 itself. The system controller 24 may also execute various signal processing and filtration functions with regard to the acquired image signals, such as for initial adjustment of dynamic ranges, interleaving of digital image data, and so forth.

In the embodiment illustrated in FIG. 1, system controller 24 is coupled to a rotational subsystem 32 and a linear positioning subsystem 34. The rotational subsystem 32 enables the X-ray source 12, collimator 14 and the detector 22 to be rotated one or multiple turns around the patient 18, such as rotated primarily in an x,y-plane about the patient. It should be noted that the rotational subsystem 32 might include a gantry upon which the respective X-ray emission and detection components are disposed. Thus, in such an embodiment, the system controller 24 may be utilized to operate the gantry.

The linear positioning subsystem 34 may enable the patient 18, or more specifically a table supporting the patient, to be displaced within the bore of the CT system 10, such as in the z-direction relative to rotation of the gantry. Thus, the table may be linearly moved (in a continuous or step-wise fashion) within the gantry to generate images of particular areas of the patient 18. In the depicted embodiment, the system controller 24 controls the movement of the rotational subsystem 32 and/or the linear positioning subsystem 34 via a motor controller 36.

In general, system controller 24 commands operation of the imaging system 10 (such as via the operation of the source 12, detector 22, and positioning systems described above) to execute examination protocols and to process acquired data. For example, the system controller 24, via the systems and controllers noted above, may rotate a gantry supporting the source 12 and detector 22 about a subject of interest so that X-ray attenuation data may be obtained at a variety of views relative to the subject. In the present context, system controller 24 may also includes signal processing circuitry, associated memory circuitry for storing programs and routines executed by the computer (such as routines for executing image processing techniques described herein), as well as configuration parameters, image data, and so forth.

In the depicted embodiment, the image signals acquired and processed by the system controller 24 are provided to a processing component 30 for reconstruction of images. The processing component 30 may be one or more conventional microprocessors. The data collected by the data acquisition system 28 may be transmitted to the processing component 30 directly or after storage in a memory 38. Any type of memory suitable for storing data might be utilized by such an exemplary system 10. For example, the memory 38 may include one or more optical, magnetic, and/or solid state memory storage structures. Moreover, the memory 38 may be located at the acquisition system site and/or may include remote storage devices for storing data, processing parameters, and/or routines for image reconstruction, as described below.

The processing component 30 may be configured to receive commands and scanning parameters from an operator via an operator workstation 40, typically equipped with a keyboard and/or other input devices. An operator may control the system 10 via the operator workstation 40. Thus, the operator may observe the reconstructed images and/or otherwise operate the system 10 using the operator workstation 40. For example, a display 42 coupled to the operator workstation 40 may be utilized to observe the reconstructed images and to control imaging. Additionally, the images may also be printed by a printer 44 which may be coupled to the operator workstation 40.

Further, the processing component 30 and operator workstation 40 may be coupled to other output devices, which may include standard or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

It should be further noted that the operator workstation 40 may also be coupled to a picture archiving and communications system (PACS) 46. PACS 46 may in turn be coupled to a remote client 48, radiology department information system (RIS), hospital information system (HIS) or to an internal or external network, so that others at different locations may gain access to the raw or processed image data.

While the preceding discussion has treated the various exemplary components of the imaging system 10 separately, these various components may be provided within a common platform or in interconnected platforms. For example, the processing component 30, memory 38, and operator workstation 40 may be provided collectively as a general or special purpose computer or workstation configured to operate in accordance with the aspects of the present disclosure. In such embodiments, the general or special purpose computer may be provided as a separate component with respect to the data acquisition components of the system 10 or may be provided in a common platform with such components. Likewise, the system controller 24 may be provided as part of such a computer or workstation or as part of a separate system dedicated to image acquisition.

Figure 2:
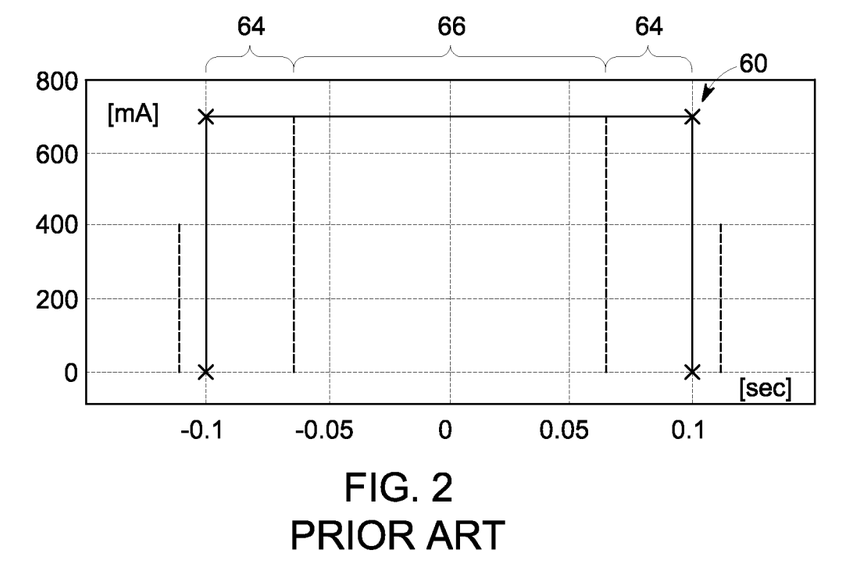
FIG. 2 depicts the integrated tube current for a full-scan run at constant X-ray tube current (mA)
Figure 3:
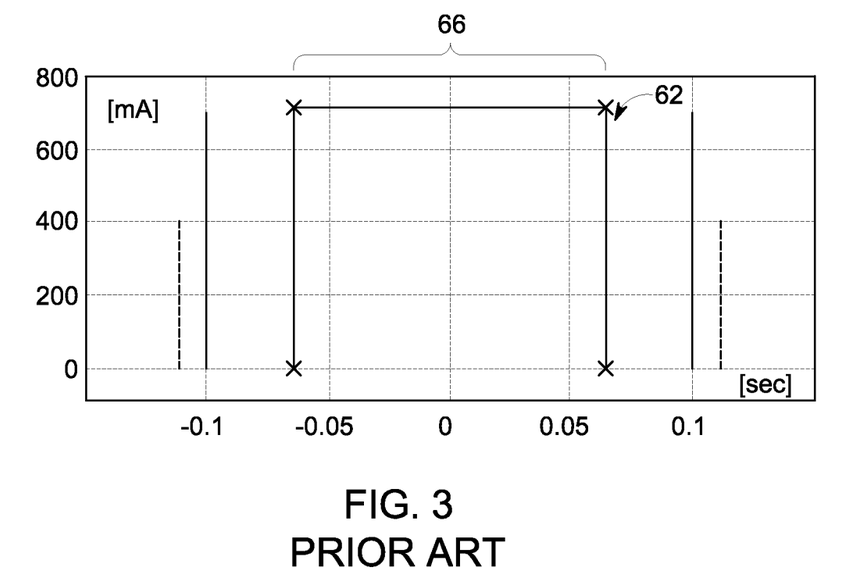
FIG. 3 depicts the integrated tube current for a half-scan run at constant X-ray tube current.

As noted above, the acquisition of image data by an imaging system, such as the depicted CT imaging system 10, is accompanied by some exposure of the patient to X-rays during the imaging process. This dose will vary depending on, among other things, whether a full-scan (i.e., a 360° rotation worth of image data views plus some possible overlap) or a half-scan (i.e., a 180° partial rotation plus the cone or fan angle of the X-ray beam) is employed during the examination. For example, turning to FIG. 2, the X-ray tube current profile is depicted for a full-scan rotation of an X-ray source about an imaging volume. Likewise, FIG. 3 depicts the X-ray tube current profile for a half-scan rotation of an X-ray source about an imaging volume. In FIGS. 2 and 3, the shaded areas represent the integrated X-ray tube current (in mAs) 60, 62 that corresponds to patient dose for the full-scan and half-scan, respectively. For a 55° fan angle, the integrated tube current 60 associated with the full-scan increases by 53% (flanking regions 64) with respect to the integrated tube current 62 associated with the half-scan. In certain embodiments, it is a goal to maintain the benefits associated with a full-scan data acquisition (e.g., reduced cone-beam artifacts) while also maintaining the temporal resolution associated with ah half-scan data acquisition (i.e., due to the reduced duration of the half-scan) while also maintaining or reducing the dose penalty relative to the half-scan case.

With respect to FIGS. 2 and 3, certain acquisition approaches acquire a full-scan of image data and attempt to preserve temporal resolution by primarily relying on the data 66 corresponding to a half-scan to reconstruct voxels in those portions of the image volume for which data is relatively complete (i.e., those regions that are always exposed to the X-ray beam). The remaining scan data (i.e., that data corresponding to flanking regions 64) is used mainly outside this region of relative data completeness but may also be used to eliminate low frequency shading artifacts (e.g., cone-beam artifacts) within the region of data completeness.

Therefore, in such approaches, it may be useful to reduce the mA associated with one or both of the flanking regions 64 to reduce the overall dose received by the patient but without significantly impacting image quality and/or temporal resolution within the region or relative data completeness. Based on this understanding, a variety of dose reducing approaches are presently contemplated.

For example, in one implementation, mA modulation may be employed within one or both of the flanking regions 64. In one embodiment a full or partial trapezoidal mA modulation is employed. For example, turning to FIG. 4, in one implementation a symmetrical or "full" trapezoidal mA profile is employed with respect to powering the X-ray source (e.g., tube) where the full mA half-scan interval 70 is sandwiched between two lower mA segments 72.

Figure 4:
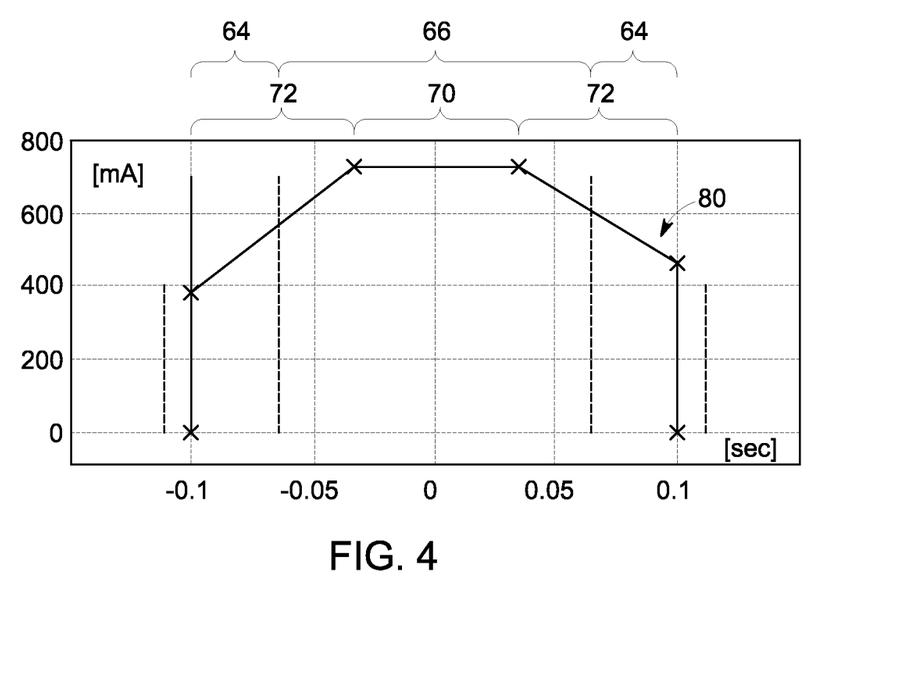
FIG. 4 depicts the integrated tube current for an implementation of a full-scan in which the X-ray tube current is modulated symmetrically with respect to a half-scan region, in accordance with aspects of the present disclosure.

While FIG. 4 depicts an embodiment in which the two lower mA segments 72 exhibit respective increasing and decreasing mA relative to a full mA half-scan interval 70, in an idealized scenario, a minimum mA would be maintained (i.e., would be constant) within the flanking regions 64 outside the half-scan region 66. However, as depicted in FIG. 4, in practice (and as depicted) it may be difficult or impossible to modulate the X-ray tube current up or down instantaneously and the falling and rising slopes reflect the X-ray tube and generator capability. Indeed, for certain scanners, mA may be increased at about 5,000 mA/second or less and may be decreased at about 4,000 mA/second or less. Thus, depending on the rise and decay time, there may or may not be a segment where the X-ray tube current is constant. Regardless, the dose the patient is exposed to is decreased in proportion to the difference between the integrated X-ray tube current areas of the full-scan scenario (shaded area 60 of FIG. 2) and the mA modulation scenario (trapezoidal area 80 (composed of areas 70 and 72 of FIG. 4)). That is, though a full-scan worth of data is acquired, the time spent at full mA (e.g., 700 mA in the depicted examples) is decreased relative to a conventional full-scan, as depicted in FIG. 2.

Figure 5:
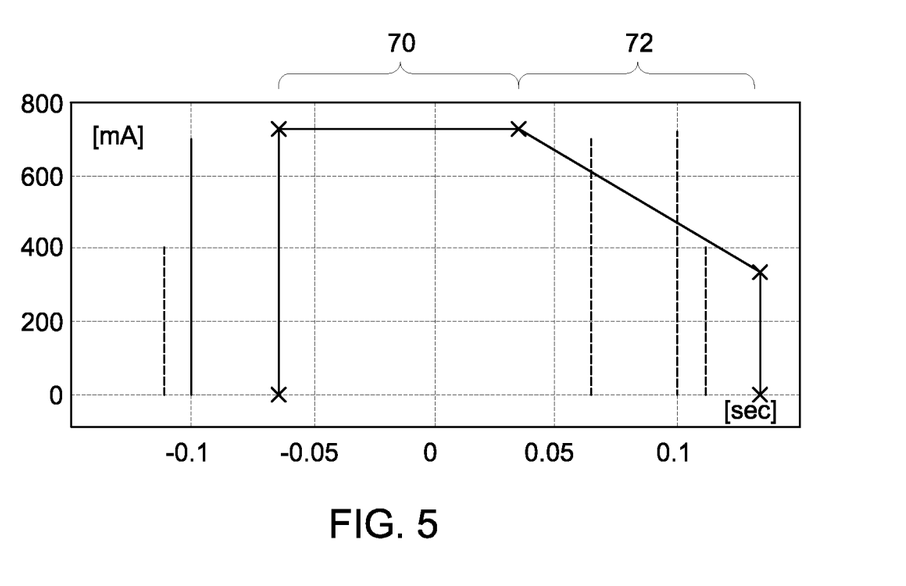
FIG. 5 depicts the integrated tube current for an implementation of a full-scan in which the X-ray tube current is modulated asymmetrically with respect to a half-scan region, in accordance with aspects of the present disclosure.
Figure 6:
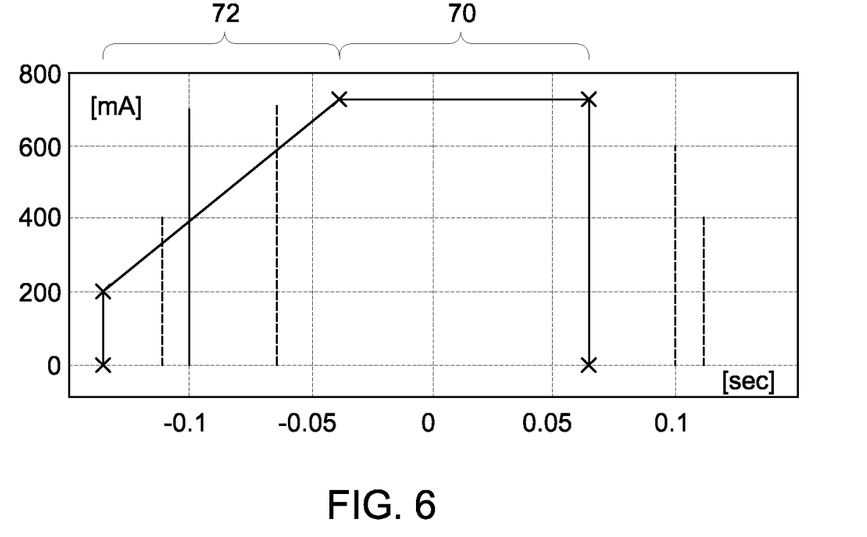
FIG. 6 depicts the integrated tube current for a further implementation of a full-scan in which the X-ray tube current is modulated asymmetrically with respect to a half-scan region, in accordance with aspects of the present disclosure.

While FIG. 4 depicts a symmetric arrangement of full mA and lower mA segments, asymmetric arrangements may also be employed. For example, turning to FIG. 5, an implementation is depicted where the X-ray tube current is initiated at full mA (segment 70) for a period corresponding to the half-scan duration (or a lightly lesser duration to reflect the speed at which mA can be decreased to the desired lower mA in the subsequent segment 72) and subsequently ramps down (lower mA segment 72) for the remaining scan duration. Conversely, in FIG. 6, an implementation is depicted where the X-ray tube current is initiated at a lower mA (segment 72) and is subsequently ramped up to full mA (segment 70) for a period corresponding to the half-scan duration (or a lightly lesser duration to reflect the speed at which mA can be increased to full mA). Thus, in these two asymmetric examples, as with the symmetric example above, a full-scan worth of data is acquired, but the time spent at full mA is decreased relative to a conventional full-scan.

As will be appreciated from the above examples, maximum mA, minimum mA, mA rise and decrease time, and duration of maximum mA are relevant parameters in configuring mA modulation protocols and define how much dose each protocol saves relative to a standard full-scan protocol. In the above examples, the full mA segment 70 was chosen to be narrower (of less duration) than the half-scan interval 66, such as for additional dose reduction and due to minimal noise impact. Further, as noted above, it depends on the relative mA modulation speed (i.e., the mA increase and/or decrease speeds) whether the low mA segments 72 reach a plateau during the scan duration. Further, asymmetric mA modulation approach such as those depicted in FIGS. 5 and 6 may save more dose than symmetric mA modulation approaches such as that depicted in FIG. 4.

While mA modulation is one approach for reducing dose, other suitable approaches may also be employed. For example, as noted above, the speed with which mA can be modulated may be limited, such as due to the finite thermal response time of an X-ray tube filament. In one implementation, instead of modulating mA (and accepting the limitations imposed by finite mA modulation speed), the X-ray tube voltage may instead be controlled to switch the X-ray tube between states (such as between 140 kV and 80 kV) where a full dose is delivered (i.e., "on") and where no or substantially no dose is delivered (i.e., "off" or "effectively off"). As will be appreciated, an "off" state of the X-ray tube or source may not necessarily correspond to 0 kVp, but may instead indicate that the tube voltage is low enough that it generates minimal or no dose to the patient.

Figure 7:
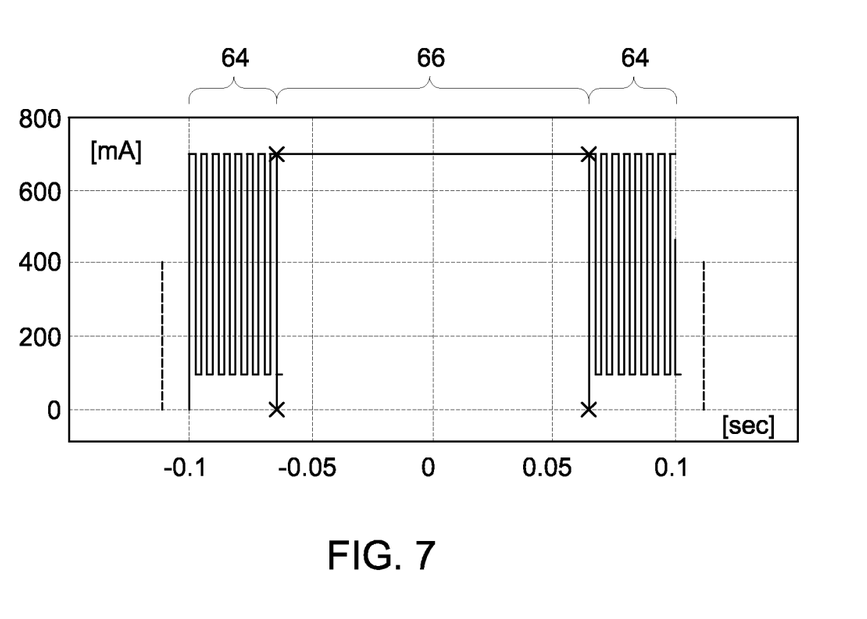
FIG. 7 depicts the integrated tube current for an implementation of a full-scan in which sparse views by changing tube voltage from high to low fast are acquired outside the half-scan region, in accordance with aspects of the present disclosure.

With this in mind, and turning to FIG. 7, one dose-reducing approach is to acquire the half-scan view range 66 at full mA and to acquire only a sparse subset of views for the remainder of the full-scan that correspond to the flanking regions 64. That is, outside the half-scan interval 66, the X-ray source may be alternated between on and off states by control of the X-ray tube voltage such that intermittent or alternating views are acquired at full mA while the interspersed views or timing is at an mA corresponding to little or no dose, i.e., no X-ray emission. Thus, only the "on" views in the flanking regions 64 are used in reconstruction. Further, only these "on" views contribute to patient dose and, thus, the overall patient dose is decreased relative to a full-scan (FIG. 2). In certain implementations, the effective spectrum of the pulsed views (i.e., the views acquired during the alternation of the X-ray tube voltage) may be different than for those views where X-ray tube voltage is not alternated. In such implementations, a dedicated calibration step may be performed to obtain the spectrum baseline for the pulsed views.

Figure 8:
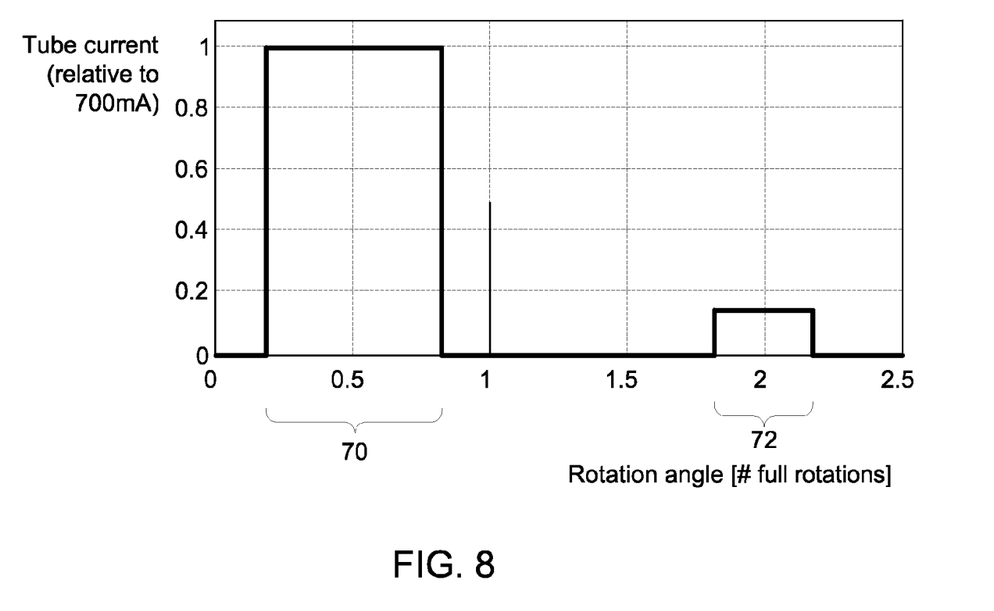
FIG. 8 depicts the integrated tube current for an implementation of a two-rotation scan where the respective data acquisitions occur at different X-ray tube currents, in accordance with aspects of the present disclosure.

Another approach to address finite mA modulation speed is to distribute the full mA segment 70 and reduced mA segments 72 over two rotations, as shown in FIG. 8. In one such embodiment, a half-scan segment 70 (i.e., 180° plus the fan angle) is performed at full mA (e.g., 700 mA) and a reduced mA segment 72 (e.g., 100 mA) is obtained with 1 rotation offset (before or after the half-scan). In one example of such an implementation time, the rotation time may be about 0.28 seconds (e.g., about a quarter of a second). The views from the two rotations are combined into a single dataset for reconstruction. In one embodiment, two-rotation approach may reduce dose (relative to a standard full-scan) more than the symmetric mA modulation approach discussed above. In two-rotation implementations, the second rotation with low mA may be used to improve the image quality in those portions of the image volume outside the region of relative data completeness as well as to reduce some low frequency shading artifacts such as cone-beam artifacts inside the portions of the image volume where data is relatively complete (i.e., those regions that are always exposed to the X-ray beam).

In one implementation, to avoid an abrupt transition, the two segments acquired in different rotations may have some angular view overlap such that they can be combined with some degree of feathering. For example, sinogram domain smoothing may be employed such that the low mA views are gradually smoothed so that the discontinuity between the low mA views and the high mA views is reduced or eliminated.

Another way to reduce X-ray dose in flanking regions 64 of a full-scan image acquisition, is to selectively collimate X-rays based on cone-angle. More specifically X-rays in the inside of the beam may be collimated or otherwise blocked, as these interior X-rays do not contribute to the corner regions of the detector region. Thus, X-rays toward the outsides of the cone, which do contribute to the corner regions, would be transmitted past the collimation. For example, a collimator blocking rows near iso-plane and letting X-rays through above a certain cone angle may be employed and a scan protocol developed where the half-scan view range is acquired without the interior cone collimation and the remainder of the scans are collected with the interior cone collimation. Again, in this manner, a scan of full-scan duration may be performed, though at a reduced effective dose to the patient due to the collimation of the interior of the cone of X-rays outside the half-scan view range.

Technical effects of the invention include acquisition of CT image data over a full-scan range (i.e., rotation) but at a dose that is reduced relative to a full scan implemented with constant X-ray tube current. Other technical effects include implementation of a full-scan CT acquisition protocol with modulation of the X-ray tube current outside of a half-scan window. Additional technical effects include implementation of a full-scan CT acquisition protocol with acquisition of sparse views outside of a half-scan window. Further technical effects include implementation of a two-rotation CT acquisition protocol to acquire image data corresponding to a single full-scan rotation, where each rotation of the two-rotation protocol employs a different X-ray tube current. Other technical effects include implementation of a full-scan CT acquisition protocol with differential z-collimation outside of a half-scan window.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of image data acquisition, comprising:
   rotating an X-ray source at least through a full rotation about an imaging volume;
   modulating an operating current of the X-ray source during the full rotation so that a first portion of the full rotation generally corresponding to a half-scan occurs at a higher operating current than a remainder second portion and a third portion of the full rotation, wherein the second portion occurs at increasing operating current and the third portion occurs at decreasing operating current;
   acquiring X-ray transmission data as the X-ray source is rotated about the imaging volume.

2. The method of claim 1, wherein the operating current is modulated such that the second portion and the third portion of the full rotation are arranged symmetrically with respect to the first portion of the full rotation generally corresponding to the half-scan.

3. The method of claim 1, wherein a dose associated with the emission of X-rays by the X-ray source during the full rotation is less than a corresponding dose obtained by rotating the X-ray source through the full rotation at the higher constant operating current.

4. A method of image data acquisition, comprising:
   rotating an X-ray source at least through a full rotation about an imaging volume;
   modulating an operating current of the X-ray source during the full rotation so that a first portion of the full rotation generally corresponding to a half-scan occurs at a higher operating current than a remainder second portion and a third portion of the full rotation, wherein the second portion occurs at increasing operating current and the third portion occurs at decreasing operating current;
   acquiring X-ray transmission data as the X-ray source is rotated about the imaging volume, wherein the operating current is modulated such that the second portion and the third portion of the full rotation are arranged asymmetrically with respect to the first portion of the full rotation generally corresponding to the half-scan.

5. A method of image data acquisition on a CT imaging system, comprising:
   rotating an X-ray source of the CT imaging system at least through one full rotation about an imaging volume;
   modulating an operating current of the X-ray source during rotation so that a first portion of the rotation generally corresponding to a half-scan occurs at a higher operating current than a remaining second portion and a third portion of the rotation, wherein the second portion occurs at increasing operating current and the third portion occurs at decreasing operating current; and
   acquiring image data corresponding to a full-scan during the rotation of the X-ray source about the imaging volume;
   wherein a dose associated with the acquisition of the image data is less than a corresponding dose associated with performing a full-scan on the CT imaging system at a constant operating current of the X-ray source.

6. The method of claim 5, wherein the operating current is modulated such that the second portion and the third portion of the rotation are arranged symmetrically with respect to the portion of the rotation generally corresponding to the half-scan.

7. A method of image data acquisition on a CT imaging system, comprising:
rotating an X-ray source of the CT imaging system at least through one full rotation about an imaging volume;
modulating an operating current of the X-ray source during rotation so that a first portion of the rotation generally corresponding to a half-scan occurs at a higher operating current than a remaining second portion and a third portion of the rotation, wherein the second portion occurs at increasing operating current and the third portion occurs at decreasing operating current; and
acquiring image data corresponding to a full-scan during the rotation of the X-ray source about the imaging volume;
wherein a dose associated with the acquisition of the image data is less than a corresponding dose associated with performing a full-scan on the CT imaging system at a constant operating current of the X-ray source, and wherein the operating current is modulated such that the second portion and the third portion of the rotation are arranged asymmetrically with respect to the portion of the rotation generally corresponding to the half-scan.

8. The method of claim 7, wherein the rotating the X-ray source at least through one full rotation about an imaging volume, comprises rotating the X-ray source through a first rotation while the X-ray source operates at a first operating current for a first set of views and rotating the X-ray source through a second rotation while the X-ray source operates at a second operating current that is less than the first operating current for a second set of views that is substantially complementary to the first set of views.

9. The method of claim 8, wherein the first set of views and the second set of views combined provide a complete set of views about the imaging volume.

10. The method of claim 7, wherein acquiring the image data corresponding to the full scan comprises acquiring sparse or incomplete views for a view range outside a half-scan view range.

11. The method of claim 10, wherein acquiring the sparse or incomplete views comprise controlling an X-ray source voltage to alternate the X-ray source between on and off states.

12. A method of image data acquisition on a CT imaging system, comprising:
rotating an X-ray source of the CT imaging system at least through one full rotation about an imaging volume;
modulating an operating current of the X-ray source during rotation so that a first portion of the rotation generally corresponding to a half-scan occurs at a higher operating current than a remaining second portion and a third portion of the rotation, wherein the second portion occurs at increasing operating current and the third portion occurs at decreasing operating current; and
acquiring image data corresponding to a full-scan during the rotation of the X-ray source about the imaging volume;
wherein a dose associated with the acquisition of the image data is less than a corresponding dose associated with performing a full-scan on the CT imaging system at a constant operating current of the X-ray source, and wherein acquiring the image data comprises collimating the X-ray source such that the X-ray source is not collimated for a first view range corresponding to a half-scan and such that the X-ray source is collimated within a central portion for a second view range outside the first view range.

13. The method of claim 12, wherein the collimator blocks X-rays near the iso-plane and allows X-rays to pass above a specified cone angle.

14. A CT imaging system, comprising:
an X-ray source configured to rotate about an imaging volume;
a detector configured to detect X-rays emitted by the X-ray source; and
a system controller configured to control operation of one or both of the X-ray source and the detector, wherein the system controller: rotates the X-ray source at least through one full rotation about the imaging volume and acquires image data corresponding to a full-scan during the rotation of the X-ray source about the imaging volume, wherein a dose associated with the acquisition of the image data is less than a corresponding dose associated with performing a full-scan on the CT imaging system at a constant operating current of the X-ray source, wherein the system controller modulates an operating current of the X-ray source during rotation so that a first portion of the rotation generally corresponding to a half-scan occurs at a higher operating current than a remaining second portion and a third portion of the rotation, wherein the second portion occurs at increasing operating current and the third portion occurs at decreasing operating current.

15. A CT imaging system, comprising:
an X-ray source configured to rotate about an imaging volume;
a detector configured to detect X-rays emitted by the X-ray source; and
a system controller configured to control operation of one or both of the X-ray source and the detector, wherein the system controller: rotates the X-ray source at least through one full rotation about the imaging volume and acquires image data corresponding to a full-scan during the rotation of the X-ray source about the imaging volume, wherein a dose associated with the acquisition of the image data is less than a corresponding dose associated with performing a full-scan on the CT imaging system at a constant operating current of the X-ray source, wherein the system controller modulates an operating current of the X-ray source during rotation so that a first portion of the rotation generally corresponding to a half-scan occurs at a higher operating current than a remaining second portion and a third portion of the rotation, wherein the second portion occurs at increasing operating current and the third portion occurs at decreasing operating current and, wherein the system controller rotates the X-ray source through a first rotation while the X-ray source operates at a first operating current for a first set of views and rotates the X-ray source through a second rotation while the X-ray source operates at a second operating current that is less than the first operating current for a second set of views that is substantially complementary to the first set of views.

16. The CT imaging system of claim 15, wherein the system controller acquires sparse or incomplete views for a view range outside a half-scan view range when acquiring the image data corresponding to the full scan.

17. A CT imaging system, comprising:
- an X-ray source configured to rotate about an imaging volume;
- a detector configured to detect X-rays emitted by the X-ray source;
- a system controller configured to control operation of one or both of the X-ray source and the detector, wherein the system controller: rotates the X-ray source at least through one full rotation about the imaging volume and acquires image data corresponding to a full-scan during the rotation of the X-ray source about the imaging volume, wherein a dose associated with the acquisition of the image data is less than a corresponding dose associated with performing a full-scan on the CT imaging system at a constant operating current of the X-ray source, wherein the system controller modulates an operating current of the X-ray source during rotation so that a first portion of the rotation generally corresponding to a half-scan occurs at a higher operating current than a remaining second portion and a third portion of the rotation, wherein the second portion occurs at increasing operating current and the third portion occurs at decreasing operating current; and
- a collimator that collimates the X-ray source such that the X-ray source is not collimated for a first view range corresponding to a half-scan and such that the X-ray source is collimated within a central portion for a second view range outside the first view range.

* * * * *